United States Patent [19]

Tohyama et al.

[11] Patent Number: 5,340,788
[45] Date of Patent: Aug. 23, 1994

[54] DIPHENYLSULFONE DERIVATIVES AND HEAT SENSITIVE RECORDING MATERIALS

[75] Inventors: Takafumi Tohyama, Osaka; Takehiro Sato, Tokyo; Kousaku Morita, Tokyo; Masaaki Uchikawa, Tokyo; Nobuyuki Hirai, Tokyo, all of Japan

[73] Assignee: Nippon Soda Co., Ltd., Tokyo, Japan

[21] Appl. No.: 842,093

[22] PCT Filed: Jul. 16, 1991

[86] PCT No.: PCT/JP91/00943
§ 371 Date: Mar. 19, 1992
§ 102(e) Date: Mar. 19, 1992

[87] PCT Pub. No.: WO92/01680
PCT Pub. Date: Feb. 6, 1992

[30] Foreign Application Priority Data

Jul. 24, 1990 [JP] Japan .................. 2-193966
Jul. 2, 1991 [JP] Japan .................. 3-187017

[51] Int. Cl.$^5$ .................. C07D 303/12; B41M 5/30
[52] U.S. Cl. .................. 503/209; 503/225; 549/556; 549/558; 549/559; 549/560; 549/563
[58] Field of Search ............ 503/209, 225; 549/556, 549/558, 559, 560, 563

[56] References Cited

PUBLICATIONS

CA 116: 49023n, 1992.
CA 116: 43199c, 1992.

*Primary Examiner*—C. Warren Ivy
*Assistant Examiner*—Ba K. Trinh
*Attorney, Agent, or Firm*—Joseph C. Mason, Jr.; George B. Oujevolk; Ronald E. Smith

[57] ABSTRACT

Storing stabilizers for color image of heat sensitive recording materials, which are higher safe diphenylsulfone derivatives represented by general formula (I), and the heat sensitive recording materials using them.

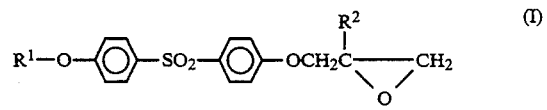

(Wherein, $R^1$ is aralkyl or lower alkenyl which may be substituted with halogen or lower alkyl and $R^2$ is hydrogen or methyl, but when $R^1$ is unsubstituted benzyl, $R_2$ is methyl).

1 Claim, No Drawings

DIPHENYLSULFONE DERIVATIVES AND HEAT SENSITIVE RECORDING MATERIALS

TECHNICAL FIELDS

This invention is concerning to novel diphenylsulfone derivatives and heat sensitive recording materials containing the compounds.

BACKGROUND ART

Many kinds of heat sensitive recording materials applying reactions of leuco chromogens with color developing materials have been commonly utilized in recording paper for output recorder of for facsimile and various instruments.

Because, it has been desired as character of the heat sensitive material to be higher sensitive for color evolution, higher whiteness of the background and higher stability of the colored image and toughness of the background concurrently, many kinds of sensitizers and stabilizers have been developed.

Sufficient material for such functions has never been found. Some compounds which were resemble to those of the present invention represented by general formula (I) but involved alkyl group such as isopropyl and glycidyl group at $R^1$ in the structure were known as adjuvant for heat sensitive recording materials. (Japanese Patent Application (unexamined) Sho 62-164579 (1987)).

The resemble compounds, above mentioned, to those in the invention have been used as storage stabilizer for color image, but their functions have been insufficient. Furthermore, they have toxicological problem such as mutagenicity. Therefore, their disadvantages in the manufacture and marketing have been in very severe circumstances according to the legal control. The purpose of the present invention is to provide a heat sensitive material with outstanding background whiteness, storage stability of the background and of the color image but without the toxicological problems above mentioned.

DISCLOSURE OF INVENTION

This invention is concerning to novel diphenylsulfone derivatives represented in general formula (1),

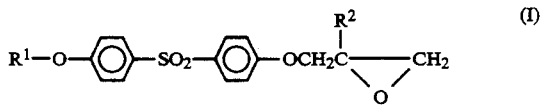
(I)

(wherein, $R^1$ is aralkyl or lower alkenyl which may be substituted with halogen or lower alkyl and $R^2$ is hydrogen or methyl, but when $R^1$ is unsubstituted benzyl, $R^2$ is methyl), and heat sensitive recording materials composing of leuco or faint color chromogens and color developers which develop color, when heated, by the reaction with the chromogens wherein the heat sensitive recording materials contain diphenylsulfone derivatives represented in general formula (I).

The compounds represented by general formula (I) exhibit outstanding excellent characteristics as adjuvant for heat sensitive recording materials and without the toxicological problem such as mutagenicity. In order to clarify the toxicological problem, the mutagenicity of compound No. 1 in the invention was tested comparing with its similar compound 4,4'-diglycidyloxydiphenylsulfone. The results showed as a reference example that the similar compound was mutagenic but no the invented compound was.

Diphenylsulfone derivatives represented by general formula (1) can be manufactured through common reactions of phenols with epichlorohydrins, that is, according to reaction equations as follows:

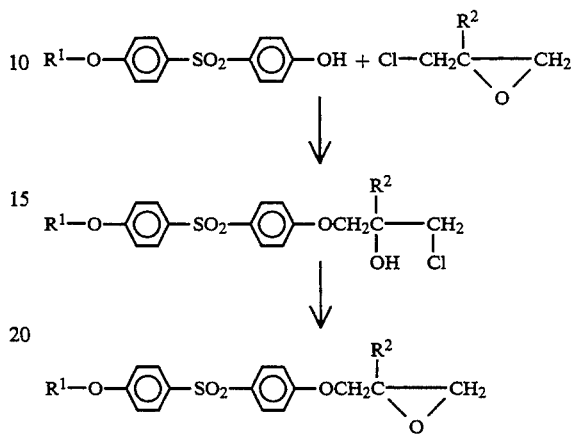

Other than the above equations, the compounds can be manufactured according to the following oxidative reaction.

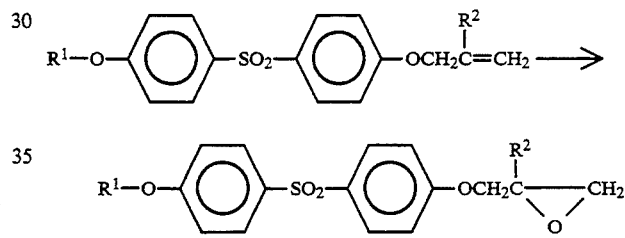

Thus synthesized compounds behave polymorphismic crystalline property. The higher melting point type crystal is obtainable from heat melted state or nearly melted state, for example, drying up, is higher melting point type. The crystal can be converted to be lower melting point crystal type by heating in polar solvents such as acetone, chloroform and etc. Additionally, mixtures of lower and higher melting point types of the crystal are possible to be prepared according to these procedures.

For example, for the compound No. 1 in the invention, the lower melting point at 158°–161° C. in example 1, on the other hand the higher melting point at 164°–167° C. in example 2 are obtained.

Typical compounds represented by general formula (I) in the invention are given as described in Table 1.

TABLE 1

| compound No. | $R^1$ | $R^2$ | Melting point °C. |
|---|---|---|---|
| (1) | ⌬–CH$_2$– | CH$_3$ | 158–161 |

TABLE 1-continued $$R^1-O-\bigcirc-SO_2-\bigcirc-OCH_2\underset{R^2}{C}-CH_2 \quad (I)$$
$$\qquad\qquad\qquad\qquad\qquad\qquad\qquad\diagdown O \diagup$$

| compound No. | $R^1$ | $R^2$ | Melting point °C. |
|---|---|---|---|
| (2) | Cl—⟨◯⟩—CH$_2$— | H | 139.5–141.0 |
| (3) | (o-Cl)⟨◯⟩—CH$_2$— | CH$_3$ | 139–145 |
| (4) | Cl—⟨◯⟩—CH$_2$— | CH$_3$ | 164–166 |
| (5) | CH$_3$—⟨◯⟩—CH$_2$— | H | 125.8–127.2 |
| (6) | CH$_3$—⟨◯⟩(CH$_3$)—CH$_2$— | CH$_3$ | 142.6–144.9 |
| (7) | CH$_2$=CH—CH$_2$— | H | 163.5–165.0 |
| (8) | naphthyl-CH$_2$— | H | 192.5–194.1 |

Although the chromogens such as fluoranes, phthalides, tactums, triphenylmethanes, phenothiazines and spiro-pyranes can be given as examples of the chromogens for heat sensitive recording materials. They are not limited in these examples. Any leuco chromogen which develops a color when it contacts with acidic color developers can be employed.

The examples of the chromogenic fluorane derivatives are given as follows:

3-diethylamino-6-methyl-7-anilinofluorane,
3-dibutylamino-6-methyl-7-anilinofluorane,
3-(N-ethyl-N-isobutylamino)-6-methyl-7-anilinofluorane,
3-(N-methyl-N-propylamino)-6-methyl-7-anilinofluorane,
3-(N-ethyl-N-isopentylamino)-6-methyl-7-anilinofluorane,
3-diethylamino-7-chloroanilinofluorane,
3-dibutylamino-7-(o-chloroanilino)fluorane,
3-diethylamino-7-dibenzylaminofluorane,
3-diethylamino-5-methyl-7-dibenzylaminofluorane,
3-(N-ethyl-p-toluidino-6-methyl-7-anilinofluorane,
3-(N-cyclohexyl-N-methylamino)-6-methyl-7-anilinofluorane,
3-pyrrolydino-6-methyl-7-anilinofluorane and
3-pyperidino-6-methyl-7-anilinofluorane.

Furthermore, any acidic substance which is possible to be applied as color developer for heat sensitive recording materials can be applied as the color developer in this case.

The heat sensitive recording materials in the invention can be prepared according to common processes. For example, coating liquid which is prepared by dispersing a diphenylsulfone, a chromogen and a color developer in the invention in aqueous solution of a hydrophilic binder were coated to supporters such as paper or plastic films and dried. Thus, the heat sensitive recording materials such as heat sensitive recording paper and etc. are obtained. When the material is prepared, a compounds in the present invention, a chromogen and a color developer are separately homogenated in each aqueous solution of a binder or it is allowed that the compound is homogenate with the chromogen or the color developer when each dispersion of the chromogen and the developer is prepared. Then these dispersions are mixed to prepare to be coating liquid.

Additionally, in the dispersion, a filler, a dispersing agent, an anti-oxidant, a desensitizer, an anti-sticking agent, a photo-stabilizer and a fluorescent bleach, etc. are allowed to be appropriately contained. Although the composition of them is variable due to the each kind of the adjuvants, usually, 1–10 weight parts, preferably, 2–5 weight parts of the color developer are used for 1 weight part of the chromogen. And, 0.5–10 weight parts, desirably 1–5 weight parts of diphenylsulfone derivative in the invention is recommendable rate for 1 weight part of the chromogen.

BEST MODE FOR CARRYING OUT INVENTION

The invention is described in detail, giving examples as follows.

Example 1

Synthesis of 4-benzyloxy-4'-(2-methylglycidyloxy)diphenylsulfone [compound (1)]

In 160 ml of chloroform, 39.4 g of 4-benzyloxy-4'-(2-methylallyloxy) diphenylsulfone was dissolved and the solution was ice cooled. In the solution, 30 g of m-chloroperbenzoic acid was slowly added and reacted under ice cooled condition for 20 hours. After the reaction, deposited m-chlorobenzoic acid was removed by filtration. The obtained chloroform layer was washed by 5% NaHO$_3$ aqueous solution and then by water. Chloroform was evaporated and residual crystal was recrystallized from toluene. Thus, 20 g of 4-benzyloxy-4'-(2-methylglycidyloxy) diphenylsulfone was obtained. Melting point of the crystal was 58°–161° C.

EXAMPLE 2

Synthesis of 4-benzyloxy-4'-(2-methylglycidyloxy)-diphenylsulfone [compound (1)] (another process)

An amount of 66 g of 2-methylepichlorohydrin, 1 g of tetrabutytammonium bromide as a catalyst and 34. 0 of 4-benzyloxy-4'-hydroxydiphenylsulfone were added and reacted at 85°–90° C. for 6 hours. After evaporating 2-methylepichlorohydrin, residual matter was dissolved in 300 ml of toluene, in which 20% sodium hydroxide aqueous solution was added, and the mixture was reacted at 80° C. for 30 minutes. After the aqueous layer was separated and discarded, the organic layer was heated at 105° C. to complete the reaction. After cooling, 4-benzyloxy-4'-(2-methylglycidyloxy) diphenylsulfone was separated by filtration and obtained as 36 g of the crystal. The melting point of the crystal was 164°–167° C.

EXAMPLE 3

Synthesis of 4-(4-methylbenzyloxy)-4'-glycidyloxydiphenylsulfone [compound (5)]

An amount of 46.3 g of epichlorohydrin, 0.8 g of tetrabutylammonium chloride as a catalyst, and 17.7 g (0.05 mol) of 4-(4-methylbenzyloxy)-4'-hydroxydiphenylsulfone were fed in four-necks flask and reacted at 100°–120 C. for 8 hours. Then, after evaporating 2-methylepichlorohydrin, residual matter was dissolved and warmed in 150 ml of toluene, in which 2 g of sodium hydroxide was added, and the mixture was reacted at 100° C. for 2 hours, followed by washing with water and filtering. The toluene solution was concentrated, then deposited crystal was filtered, dried to obtain 13.3 g of white crystal of desired compound. The melting point of the crystal was 125.8°–127.2° C. 2° C.

| Example 4 (Preparation of Heat Sensitive Recording Paper) | |
|---|---|
| Chromogen dispersion (Liquid A): | |
| 3-dibutylamino-6-methyl-7-anilinofluorane | 7.0 g |
| 15% aqueous solution of polyvinyl alcohol | 41.5 g |
| clay | 11.5 g |
| pure water | 40.0 g |
| Color developer dispersion (Liquid B) | |
| 4-isopropoxy-4'-hydroxydiphenylsulfone | 10.5 g |
| 15% aqueous solution of polyvinyl alcohol | 41.5 g |
| clay | 8.0 g |
| pure water | 40.0 g |
| Adjuvant dispersion liquid (liquid C) | |
| A compound in the invention (or a reference compound) | 7.0 g |
| 15% aqueous solution of polyvinyl alcohol | 41.5 g |
| clay | 11.5 g |
| pure water | 40.0 g |

Each above mixture was sufficiently homogenized by sand grinder to prepare Liquid A, B or C. One weight part of Liquid A, 2 weight parts of Liquid B and 1 weight part of Liquid C. were mixed to prepare a dispersion liquid to tint. The liquid was coated on white paper by applying Wire Rod No. 12, then dried to manufacture the heat sensitive recording paper.

COMPARATIVE EXAMPLE 1.

In the preparation of Liquid C in Example 4, instead of the compound in the invention, 4-glycidyloxy-4'-isoprpoxydiphenylsulfone was taken place, the other components were same as Example 4 and the heat sensitive recording paper was similarly prepared.

Reference Example 2.

In the preparation of Liquid C in Example 4, instead of the compound in the invention, clay was taken place, the other components were same as Example 4 and the heat sensitive recording paper was similarly prepared.

Test Example 1.

A part of the heat sensitive recording papers which were prepared according to the Example 4 and the Comparative examples were heated from both sides to develop color at 150° C. by dry-heating tester (Kishino Science machinery Co.). Then, after they were placed in Incubator Controlled Humidity and Temperature at 50° C. under 80% humidity and in Fademeter (Type FAL-5, Suga Tester Co.) exposing for 3 hours, the stability of backgrounds, of the color images and antiphoto stability were determined by Macbeth Reflection Densitometer (Type RD-514, Ratten #106).

The results are shown in Table 2.

TABLE 2

| No. of Compounds in the invention | Stability of Background to heat and humidity | | Photostability of developed image | |
|---|---|---|---|---|
| | Before exposing | After exposing | Before exposing | After exposing |
| (1) | 0.06 | 0.07 | 1.21 | 1.13 |
| (2) | 0.07 | 0.11 | 1.23 | 1.15 |
| (3) | 0.08 | 0.10 | 1.22 | 1.09 |
| (4) | 0.07 | 0.09 | 1.23 | 1.14 |
| (5) | 0.08 | 0.10 | 1.20 | 1.12 |
| (6) | 0.09 | 0.12 | 1.22 | 1.16 |
| (7) | 0.07 | 0.07 | 1.21 | 1.12 |
| Comparative example 1* | 0.07 | 0.17 | 1.19 | 1.00 |

*Used adjuvant is 4-glycidyloxy-4'-isopropyldiphenylsulfone.

Test Example 2.

The heat-sensitive recording papers prepared in Test example 4 and Reference examples were unsatisfactorily colored to be a checker pattern. Film wrapped by polyvinyl chloride was closely touched on their both sides. Plasticizer proofness in such state was tested by keeping in dark room at 25° C. (the room temperature) for 10 days. The color density before and after exposing for these tests was determined by Macbeth Reflection Densitometer (RD-514) through a filter (#106). The results are shown in Table 3.

TABLE 3

| No. of Compounds in the invention | Concentration of colored image | | Remained |
|---|---|---|---|
| | Before exposing | After exposing | % |
| (1) | 0.77 | 0.54 | 70 |
| (3) | 0.76 | 0.34 | 45 |
| (4) | 0.77 | 0.35 | 45 |
| (5) | 0.88 | 0.56 | 64 |
| (6) | 0.83 | 0.53 | 65 |
| (7) | 0.89 | 0.56 | 60 |
| Comparative example 2* | 0.79 | 0.18 | 23 |

*no adjuvant

Reference Example. (Mutagenic Property)

Mutagenic activity of the compound No. 1 in the invention and 4,4'-diglycidyldiphenylsulfone was evaluated by Ames test for using Salmonela strains (TA-100 and TA-1535) and E. coli (WP2uvrA) under conditions of metabolic activation and metabolic inactivation. The metabolic activation system was consisted of supernatant of 9000 G in centrifugation from rat liver homogenate (S9) mixture which was induced by 5,6-benzoflavone or phenobar bital, and a coenzyme. Both test compounds were prepared at concentration of 50 mg/mL by using dimethylformamide. Then, they were successively diluted to prepare lower concentration solutions by the same solvent. The concentration of each test substance is adjusted to be 128, 320, 800, 2000 and 5000 µg/plate. The test mixture of the bacteria, each test substance and sodium phosphate buffer solution (S9 mixture under the metabolic activation condition) was incubated at 37° C. for 20 minutes. After the incubation the mixture was added by soft agar solution containing minimum nutrients, homogeneously inoculated on an agar plate and incubated at 37° C. for 65 hours. After the incubation deposited materials were observed at higher concentration than 800 μg/plate for the compound No. 1 in the invention and at higher concentration than 320–800 μg/plate for 4,4'-diglycidyldiphenylsulfone under both conditions of the metabolic activation and such inactivation. No increase of recovery mutation colony was observed in any strain for the compound No. 1 in the invention, on the other hand increases of recovery mutation colony were in all strains for 4,4'-diglycidyldiphenylsulfone. It was concluded from the results that the compound No 1. was not mutagenic, but 4,4'-diglycidyldiphenylsulfone was mutagen.

Industrial Applicability

Effect of the Invention

The heat sensitive recording paper using compounds in the invention has outstanding superiority with respects to its storing stability, toughness of the background, especially anti-photolysis and antiplastic properties, furthermore, no toxicology problem such as mutagenicity.

We claim:

1. Heat sensitive recording material containing chromogen, color developer, and diphenylsulfone derivative of the formula (I)

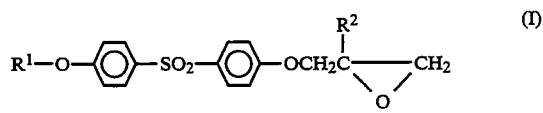

wherein $R^1$ is lower alkenyl or aralkyl optionally substituted with halogen or lower alkyl, and $R^2$ is hydrogen or methyl with the proviso: when $R^1$ is unsubstituted benzyl, $R^2$ is methyl.

* * * * *